US008986776B2

(12) United States Patent
Sandmeier et al.

(10) Patent No.: US 8,986,776 B2
(45) Date of Patent: Mar. 24, 2015

(54) METHOD FOR PRODUCING AN ANTIMICROBIAL COATING ON A TECHNICAL SURFACE

(75) Inventors: Dieter Sandmeier, Uttenreuth/Weiher (DE); Theresa Sandmeier, legal representative, Uttenreuth/Weiher (DE); Barbara Maria Sandmeier, legal representative, Furth (DE); Ulrich Matthias Sandmeier, legal representative, Dormitz (DE); Stephan Maximillian Sandmeier, legal representative, Uttenreuth/Weiher (DE); Eva Kensbock, Munich (DE)

(73) Assignee: Fraunhofer-Gesellschaft zur Förderung der Angewandten Forschung e.V., Munich (DE)

( * ) Notice: Subject to any disclaimer, the term of this patent is extended or adjusted under 35 U.S.C. 154(b) by 534 days.

(21) Appl. No.: 13/238,040

(22) Filed: Sep. 21, 2011

(65) Prior Publication Data

US 2012/0076919 A1 Mar. 29, 2012

Related U.S. Application Data

(63) Continuation-in-part of application No. 11/917,154, filed on Jul. 23, 2008, now abandoned.

(30) Foreign Application Priority Data

Jun. 13, 2005 (DE) ......................... 10 2005 027 347
Mar. 24, 2006 (WO) ................. PCT/EP2006/002701

(51) Int. Cl.

*B05D 5/00* (2006.01)
*B05D 3/12* (2006.01)
*A01N 25/10* (2006.01)
*A01N 37/06* (2006.01)
*A01N 37/10* (2006.01)
*A01N 43/90* (2006.01)
*C09D 5/16* (2006.01)

(52) U.S. Cl.

CPC ................ *A01N 25/10* (2013.01); *A01N 37/06* (2013.01); *A01N 37/10* (2013.01); *A01N 43/90* (2013.01); *C09D 5/1625* (2013.01)

USPC ......... 427/2.1; 427/532; 427/535; 427/385.5; 427/299; 427/314; 427/290; 427/307

(58) Field of Classification Search

USPC ............... 427/2.1, 532, 535, 385.5, 299, 314, 427/290, 307

See application file for complete search history.

(56) References Cited

U.S. PATENT DOCUMENTS 6,403,113 B1 6/2002 Corzani
6,506,737 B1 1/2003 Hei et al.
2004/0219128 A1 11/2004 Batdorf

FOREIGN PATENT DOCUMENTS

EP 0 986 965 3/2000
EP 0 986 965 A1 * 3/2000 ............. A23L 1/317
WO WO 2004/052961 A1 6/2004
WO WO 2004/105491 A1 12/2004

* cited by examiner

*Primary Examiner* — Robert D. Harlan

(74) *Attorney, Agent, or Firm* — Antonelli, Terry, Stout & Kraus, LLP.

(57) ABSTRACT

The invention relates to a method for producing a microbial substance-releasing layer on a technical surface. The inventive method comprises three steps: a) producing a solution from polyvinylacetate, a preservative agent and a solvent, b) applying the solution to the technical surface, and c) drying the solution applied to the technical surface while forming the layer. The inventive method is characterized by using benzoic acid, sorbic acid, natamycin, bacteriocines, plant extracts or mixtures thereof as the preservative agent and an ethanol/ water mixture, ethyl acetate or acetone as the solvent.

15 Claims, No Drawings

METHOD FOR PRODUCING AN ANTIMICROBIAL COATING ON A TECHNICAL SURFACE

CROSS REFERENCE TO RELATED APPLICATION

This application is a Continuation-in-Part of U.S. patent application Ser. No. 11/917,154, filed on Jul. 23, 2008 now abandoned, entitled "Method for Producing An Antimicrobial Coating on a Technical Surface," which application is incorporated herein by reference in its entirety.

BACKGROUND OF THE INVENTION

1. Field of the Invention

The invention relates to a method for producing an antimicrobial coating on a technical surface.

2. Description of the Prior Art

Antimicrobial coatings of the above-mentioned type are used in an intrinsically known manner in food packaging materials for protecting the packed food products from attack by microorganisms such a bacteria, fungi or other germs. Perishable food products in particular can be stored for a long time in a high quality condition when packaging materials with an antimicrobial coating are used. In addition, the risk of the occurrence of pathogens on or in the packed food products is reduced.

Antimicrobial coatings typically have a carrier layer in a matrix design with active substances or inhibitors embedded therein, which, upon contact with microorganisms, kill them or inhibit or prevent their growth. At present two principles of operation of antimicrobial coatings are essentially known:

The first principle of operation is that the antimicrobial active substances and inhibitors have volatile properties and are first embedded in a carrier layer of a matrix design, but are released in time from the matrix material. The antimicrobial action therefore takes place not only in the close region above the coated surface, but the active substances and inhibitors develop their antimicrobial action throughout the packaging volume by release from the carrier layer. Suitable antimicrobial active substances for this principle of operation may be used for food applications in the European area (for example chlorine dioxide, since it is toxic, or ethanol, since it has adverse sensory properties).

The second principle of operation is significantly more widespread and is that the antimicrobial active substances and inhibitors are spatially fixed in the carrier layer in such a manner that they not able to escape from the carrier layer independently. The antimicrobial action of the active substances and inhibitors embedded in the coating material of a matrix design is developed, in particular, by contact of the food products with the antimicrobially coated surface. Here the active substances and inhibitors can diffuse through the surface of the matrix material into the surface of the food product so that the antimicrobial action of the coating is determined essentially by the diffusion kinetics.

With regard to the packing of food products with antimicrobially coated food packaging materials, a multiplicity of active substances and inhibitors, as well as release mechanisms, have been investigated in recent years. The publication: 'Review of Antimicrobial Food Packaging', by Paola Appendini and Joseph H. Hotchkiss, in Innovative Food Science & Emerging Technologies 3 (2002) 113-126, gives an overview of these substances.

However, the methods of the prior art for producing an antimicrobial coating suffer from the disadvantage that the coating is either technically complicated to produce, and is therefore expensive, or the raw materials used are not available in sufficient quantity or the raw materials and/or the resultant product substances do not meet the legal requirements.

SUMMARY OF THE INVENTION

The invention is a low cost method for producing an antimicrobial coating on a technical surface, which method is technically simple and meets the existing legal requirements. It will be possible, in particular, to implement the invention in the production of antimicrobial coatings on food packaging materials and on technical surfaces which are of relevance in medicine, the pharmaceutical industry, biology, in consumer goods, in the household or in the textile industry, and which are to be protected from colonization by microorganisms such as bacteria, fungi or germs. It will also be possible to carry out the method with conventional systems, which means that coating systems already in use may be resorted to.

A method for producing a carrier layer disposed on a technical surface which releases at least one antimicrobial substance for inhibiting growth of microorganisms comprising producing a solution from polyvinyl acetate, a preservative agent and a solvent; pretreating the technical surface to enhance adhesion power of the technical surface, applying the solution to the technical surface; and drying the solution applied to the technical surface while forming the layer; and wherein the technical surface comprises one of a film, a product produced from plastic, a product produced from paper, a product produced from metal, a packaging material or an agent used in a field of medicine.

The method is used in the food and packaging industry, in particular for packing perishable food products. It is also possible to apply the method in all fields in which it is necessary to protect surface regions from contamination with bacteria, fungi, ricksettia or germs, e.g. in medicine, the pharmaceutical industry, biology, in consumer goods, in the household or in the textile industry.

The inventive method is essentially described by three method steps:

a) a producing a solution which has, in fully dissolved form: polyvinyl acetate, a preservative agent and a solvent;

b) applying the solution to the technical surface; and c) drying the solution applied to the technical surface while forming the antimicrobial layer.

In the first method step, a solution is produced which has the components polyvinyl acetate, a preservative agent and a solvent. One hundred percent ethyl acetate, or preferably an ethanol-water mixture with an ethanol/water mixing ratio of between 80:20 and 100:0 percent by weight is used as the solvent. The ethanol-water mixture serves as a technical, physiological and environmentally harmless solvent which can be evaporated and largely recovered. Acetone is also suitable as a solvent.

Polyvinyl acetate is first added to the solvent and completely dissolved in the solvent. Polyvinyl acetate has been shown to be an ideal substance for the matrix-type carrier layer of the antimicrobial coating to be produced, since it is easily soluble in a solvent, has very good release properties as a carrier layer for the antimicrobial active substances or inhibitors embedded in it, and forms a transparent, flexible, film-like carrier layer after it is applied to a technical surface. The solution preferably contains up to 60 percent by weight of polyvinyl acetate related to the quantity of solvent.

The preservative agent is then added to the solvent. The preservative agent corresponds to the actual antimicrobial active substance or inhibitor. In principle a multiplicity of such active substances or inhibitors that can be used in this method are known (cf. Paola Appendini and Joseph H. Hotchkiss, Innovative Food Science & Emerging Technologies 3 (2002), page 115, Table 2). Benzoic acid, sorbic acid, natamycin, bacteriocines (for example, nisin or pedicin), plant extracts or mixtures thereof have proved to be ideal active substances of inhibitors. Benzoic acid and sorbic acid in particular are legally licensed both for food products and for plastics used for food packaging and have a broad antimicrobial spectrum of action against different groups of microorganisms, for example bacteria, yeasts or moulds. In polyvinyl acetate films both these substances also remain dissolved up to high concentration ranges without their affecting the transparency of the polyvinyl acetate films due to their own crystallisation. As indicated, however, other well known preservative agents or mixtures thereof, licensed according to food legislation, may also be used. The solution, with the components solvent, polyvinyl acetate and preservative agent, preferably contains up to 40 percent by weight of preservative agent related to the quantity of polyvinyl acetate contained in the solution.

Furthermore a so-called activity regulator can be added to the solution and has the function of setting the pH value of the technical surface and its immediate surroundings so that the preservative agent or agents is or are present in the solution in undissociated form. The preservative agents which correspond to the active substances or inhibitors, as mentioned above, can develop their antimicrobial action to the optimum degree in undissociated condition. The use of lactic acid or citric acid as an activity regulator has surprisingly proved particularly suitable when combined with benzoic and/or sorbic acid. The solution preferably contains up to 5 percent by weight of the activity regulator related to the quantity of preservative agent contained in the solution.

The solution is preferably produced with continuous agitation, maintaining a temperature level ranging between 20 and 50° C. ideal for producing the solution.

In the second method step, the mixed and, if necessary, tempered solution is applied to the technical surface. All the methods and techniques available for the specific application of a liquid medium to a technical surface are considered for this purpose, for example dipping, printing, painting or spraying methods and application of the solution by means of brushes, spreading knifes or fluted rollers. The technique to be selected for applying the solution depends on the condition of the surface to be coated and the shape of the body having the surface. Conventional painting methods may be used for coating polymer films or paper, for example, whereas spraying techniques are more suitable for beaker-shaped containers.

It has been recognized as particularly advantageous if technical surfaces with a preferred electrical surface polarity suitable for an internal composite between the surface and solution. The electrical polarity of technical surfaces may be produced or varied by electrical fields. The electrical polarization of the technical surface preferably takes place before application of the solution by means of corona discharge or comparable methods of plasma enhanced surface reaction. Preferably such methods of plasma enhanced surface reaction are executed at atmospheric conditions or at lower pressure conditions, for example 0.1-100 Pascal. The term “atmospheric conditions” means conditions under ambient atmospheric pressure which means that no elevated pressure conditions are necessary. For example plasma jet or barrier discharge techniques are suitable.

To enhance the internal composite between the surface and solution it is alternatively recognised to pre-treat the technical surface before application of the solution by at least one of the following means of a) flame treatment, especially applied on OPP-foils (oriented polypropylene foil), which produces polar groups at the technical surface b) mechanical treatment to enlarge the technical surface, for example roughening the surface by grinding the surface, c) applying an adhesion promoter onto the technical surface, for example a primer solution containing a low solid rate for realizing a thin primer coating onto the technical surface of less nanometers thickness or d) chemical treatment to enlarge the technical surface by means of etching or fluorination of the technical surface to produce at least partially a flour layer onto said technical surface In the third method step the solution applied to the technical surface is dried at temperatures below 60° C. As a result of drying the solvent is liquefied with the formation of the matrix-type carrier layer, consisting of polyvinyl acetate, with the preservative agents embedded in it, i.e. the antimicrobial active substances or inhibitors.

An antimicrobial coating can therefore be produced on a technical surface by the method of the invention, which surface has polyvinyl acetate as the carrier layer, with one or a plurality of antimicrobial active substances or inhibitors embedded therein, which are released in time from the matrix material. Surfaces of food packaging materials, particularly film surfaces and/or containers produced from plastic, paper, metal or natural substances, are considered as technical surfaces for this purpose. Moreover, the coating according to the invention may also be used for technical surfaces in the areas of medicine, the pharmaceutical industry, biology, in consumer goods, in the household or in the textile industry, surfaces which are to be protected against colonization by microorganisms such as bacteria, fungi or other germs.

It is also possible, with the method of the invention, to apply antimicrobial coatings to technical surfaces by simple, conventional technical means using low cost raw materials available in any quantity and licensed according to the food legislation.

DESCRIPTION OF THE INVENTION

The invention is described in the following, without limiting the general inventive concept, with reference to a following exemplary embodiment.

First a clear solution is produced from 10 g of polyvinyl acetate, which is available in powder form or as a granulate, and 100 g of a solvent consisting of a mixture of ethanol and water in a mixing ratio of 95:5% by weight, with agitation and heating to 30-40° C., so that the polyvinyl acetate is present in fully dissolved form. Ten percent by weight of sorbic acid (preservative agent), related to the polyvinyl acetate contained in the solution, that is 1 g of sorbic acid, and 0.1% by weight of lactic acid, related to the quantity of preservative agent contained in the solution, i.e. 0.001 g of lactic acid, are then added to the solution. After a short time a clear solution is formed. The solution is now applied to a carrier film consisting of polyolefins, and spread on its surface by means of a spreading knife. Depending on the spreading knife used, coat thicknesses of the applied solution of between 40 and 100 μm were produced in this case. For better adhesion of the applied solution to the carrier film it is advantageous to generate a surface tension of approximately 40 dynes/cm$^2$ on the carrier film by means of a corona process before applying the solution. In the case of the carrier film of polyolefins used here, this results in improved adhesion properties between the film and the applied solution.

The solution applied to the carrier film is now dried at a temperature of 50° C. for approximately 5 minutes. Further parameters, such as the quantity of air supplied or the humidity, must be taken into consideration according to the drying process used. A temperature of 60° C. as a temperature limit should not be exceeded during the drying process. During drying a transparent, flexible coating is formed on the polymer film. After cooling, its antimicrobial action can be tested, for example, in a modified agar diffusion test which comprises the following four steps:

1. Supplying a Petri dish with a sterile agar layer,
2. Placing the test film with coated and uncoated areas onto the agar layer,
3. Applying agar, which contains a test germ, to the test film,
4. Incubation and evaluation.

The antimicrobial polyolefin film, that is the film coated with the solution, in the agar diffusion test described using the test organism saccharomyces cerevisiae, shows that no colonizations of microorganisms occur in the coated surface region of the test film. Coated films produced by the method described above also exert their inhibiting action against microorganisms of the type bacteria, gram positive and gram negative, fungi and other areas of microbiology. It was also shown by measurements that the coatings examined release approximately 20-40 mg/m$^2$ of the preservative agents used in 2 days.

The invention claimed is:

1. A method for producing a carrier layer disposed on a technical surface which carrier layer releases at least one antimicrobial substance for inhibiting growth of microorganisms comprising:

producing a solution from polyvinyl acetate, a preservative agent and a solvent;

pretreating the technical surface to enhance adhesion power of the technical surface and applying the solution to the technical surface; and drying the solution applied to the technical surface while forming the layer; and wherein the technical surface comprises one of a film, a product produced from plastic, a product produced from paper, a product produced from metal, a packaging material for food or an agent used in a field of medicine.

2. The method according to claim 1, wherein:

the technical surface is pre-treated by electrically polarization before the solution is applied to the technical surface by means of plasma enhanced surface reaction.

3. The method according to claim 1, wherein:

the technical surface is pre-treated by flame treatment before the solution is applied to the technical surface.

4. The method according to claim 1, wherein:

the technical surface is pre-treated by mechanical treatment for enlarging the technical surface before the solution is applied to the technical surface.

5. The method according to claim 4, wherein:

mechanical treatment of the technical surface is effected by roughening the technical by means of grinding.

6. The method according to claim 1, wherein:

the technical surface is pre-treated by applying an adhesion promoter onto the technical surface before the solution is applied to the technical surface.

7. The method according to claim 6, wherein:

applying the adhesion promoter is effected for producing a thin primer coating onto the technical surface of less nanometers thickness.

8. The method according to claim 1, wherein:

the technical surface is pre-treated by chemical treatment to enlarge the technical surface by means of etching.

9. The method according to claim 1, wherein:

the technical surface is pre-treated by fluorination of the technical surface.

10. The method of claim 1, wherein:

the technical surface comprises a film.

11. The method of claim 1, wherein:

the technical surface comprises a product produced from plastic.

12. The method of claim 1, wherein:

the technical surface comprises a product produced from paper.

13. The method of claim 1, wherein:

the technical surface comprises a product produced from metal.

14. The method of claim 1, wherein:

the technical surface comprises a packaging material.

15. The method of claim 1, wherein:

the technical surface comprises an agent used in field of medicine.

* * * * *